(12) United States Patent
Bai et al.

(10) Patent No.: US 8,383,808 B2
(45) Date of Patent: Feb. 26, 2013

(54) METHOD TO PREPARE D-GLUCOSAMINE HYDROCHLORIDE

(76) Inventors: Jianguo Bai, Nantong (CN); Degui Wang, Nantong (CN); Jian Wang, Nantong (CN)

( * ) Notice: Subject to any disclaimer, the term of this patent is extended or adjusted under 35 U.S.C. 154(b) by 135 days.

(21) Appl. No.: 12/904,161

(22) Filed: Oct. 14, 2010

(65) Prior Publication Data
US 2012/0095204 A1 Apr. 19, 2012

(51) Int. Cl.
*C08B 37/00* (2006.01)
*C07H 5/04* (2006.01)
*C07H 5/06* (2006.01)

(52) U.S. Cl. ..................................................... 536/55.3
(58) Field of Classification Search .................. None
See application file for complete search history.

(56) References Cited

FOREIGN PATENT DOCUMENTS

| CN | 200810238484.8 | 5/2009 |
| CN | 200810088877.5 | 10/2009 |

OTHER PUBLICATIONS

Zhang et al. CN 101628921, published Jan. 20, 2010, machine translation.*
Yan et al. CN 101429221, published May 13, 2009, machine translation.*

* cited by examiner

*Primary Examiner* — Layla Bland
(74) *Attorney, Agent, or Firm* — Allen (Zhi Yang) Xue; Anova Law Group, PLLC

(57) ABSTRACT

A method to prepare D-glucosamine hydrochloride, obtaining product from raw material of citric acid residue from citric acid production by means of fermentation, and through processes of hydrolysis, suction filtering, concentration etc. Due to recovery of the citric acid residue, the present invention alleviates the environment pollution caused by the residue; Moreover, the D-glucosamine hydrochloride product produced from the raw material of citric acid residue is vegetarian D-glucosamine hydrochloride, without fishy odor and heavy metal pollution, safe and environment-friendly, with product purity up to 98-102%, and in line with the U.S. Pharmacopeia (USP) $32^{nd}$ edition quality standards; Meanwhile, due to sufficient resources of the raw material, there is no limitation of resources for production, and production cost is low; the present invention further saves the cost to treat environment pollution and has a good effect of recycling economy; More importantly, it overcomes people's bias in this technical field, reduces the time of hydrolysis reaction, and enhances product output and production efficiency while ensuring a high product purity.

6 Claims, No Drawings

METHOD TO PREPARE D-GLUCOSAMINE HYDROCHLORIDE

BACKGROUND OF INVENTION

1. Field of the Invention

The present invention relates generally to the field of D-glucosamine hydrochloride, and more particularly to a method to prepare D-glucosamine hydrochloride using citric acid residue.

2. Description of Related Art

Citric acid is a widely used organic acid, and can be used as sour agent, thickening agent, or cleaning agent. It is commonly used in food, beverage, medical, chemical and detergent industries. Stimulated by export, the output of citric acid in China increased from 380,000 tons in 2001 to 700,000 tons in 2005, and nearly 800,000 tons in 2006. With an annual growth of 12.5%, China has become the biggest citric acid producing country, accounting for 70% of the global output. However, at present most manufacturers are still preparing citric acid in the method of fermentation, and during the process, vast amounts of citric acid residue are directly discharged without comprehensive utilization.

D-glucosamine hydrochloride (molecular formula: $C_6H_{13}NO_5 \cdot HCl$), is a white crystal, odorless and slightly sweet, easily soluble in water, slightly soluble in methanol and insoluble in organic solvents like alcohol. D-glucosamine hydrochloride is a basic unit of many significant polysaccharides in biological cells, and is an important precursor to synthesize bifidus factors. Having many important physiological functions in an organism, it is mainly used clinically to enhance functions of the body's immune system, and to constrain overgrowth of cancer cells or fiber cells, offering functions of inhibiting and curing cancers and malignant tumors; it is also effective in curing various inflammations. Moreover, because glucosamine can prevent accumulation of cholesterol in the body, long-term usage of glucosamine can have a good anti-aging effect. At present, D-glucosamine hydrochloride is the newest $3^{rd}$-generation sanitarian functional food additive in tunicin health food series, and can be used as a food antioxidant, infant food additive, low caloric sweetener for diabetics, or a food additive to fight or prevent cancer, or lower blood fat and blood pressure; Meanwhile, D-glucosamine hydrochloride is also used in the medical industry, for example, as a biochemical reagent to synthesize medicines, or as an antibacterial and immune adjuvant. It is an activating agent for the body to fight influenza virus. D-glucosamine can also be used in food, cosmetics and feed additives, offering wide application fields.

At present, the traditional method to produce D-glucosamine hydrochloride is chitin preparation, i.e., firstly extracting chitin or chitosan from lobster or crab shells, and then obtaining D-glucosamine hydrochloride through hydrolysis with hydrochloride. This preparation method has the following main disadvantages:

Firstly, D-glucosamine hydrochloride extracted from shells of aquatic products is not suitable for patients allergic to aquatic products;

Secondly, the purification process is complicated, and the product has a fishy odor and is unstable;

Thirdly, due to pollution of ocean environment, D-glucosamine hydrochloride extracted from lobster and crab shells is inevitably subject to heavy metal pollution.

In order to overcome the shortcomings of the above production method, there has been some public patents prior to the present invention in relation to preparation of D-glucosamine hydrochloride from citric acid residue, such as China patent applications CN200810088877.5 and CN200810238484.8. However, inventors of these patents all have a mistaken concept that the volume concentration of hydrochloric acid and temperature of the hydrolysis reaction can not be too high at the same time, especially the temperature of the hydrolysis reaction shall not be over 90° C., otherwise it will cause carbonization of the citric acid residue, and consequently lead to lower output. On the other hand, when reaction takes place at a temperature lower than 90° C., the reaction time will be much longer. Generally, it takes more than 10 hours for each complete reaction, and therefore production efficiency is greatly reduced.

SUMMARY OF INVENTION

To solve the above identified problem, the purpose of the present invention is to provide a method to prepare D-glucosamine hydrochloride. Such a method can help to recover citric acid residue and alleviate environmental pollution caused by the residue, and meanwhile, the product made from citric acid residue as raw material is vegetarian D-glucosamine hydrochloride, safe and environment-friendly. It features lower production cost, and a good effect of recycling economy, more importantly, it overcomes people's bias in this technical field by increasing the hydrolysis reaction temperature to over 90° C., contributing to higher reaction speed and higher product yield.

To the above purposes, the present invention adopts the following technical solution: A method to prepare D-glucosamine hydrochloride, comprising the following steps:

(1) Hydrolysis: Pump hydrochloride with mass concentration of 30%~35% into the reactor, heat to 60~70° C. with steam, then input citric acid residue, heat to 90~105° C. with steam, maintain hydrolysis reaction for 2~5.5 hours, wherein, citric acid residue:hydrochloride (weight ratio)=1:1.6~2.5;

(2) Suction filtering: Put the material after the above hydrolysis into a suction filtering barrel for suction filtering, and rinse the filter residue after the suction filtering with running water for 2~3 times, and then wash it with dilute alkali of 1%~3% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 25~35° C., and then transfer it into a centrifugal machine for centrifugal separation to obtain solid substance, which is crude D-glucosamine hydrochloride.

Moreover, to increase purity of D-glucosamine hydrochloride, the present invention also includes the following steps to process the above D-glucosamine hydrochloride crude:

(4) Purification:

a. Put the post-centrifugation crude product into a primary purifier, input deionized water, steam heat to 80~95° C., input active carbon and maintain reaction for 0.5~1.5 hours, obtain mother solution through suction filtering and transfer it into a primary cooler for natural cooling till the temperature goes down to 25~35° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, steam heat to 80~95° C., input active carbon and maintain reaction for 0.3~1.5 hours, obtain mother solution through suction filtering and transfer it into a secondary cooler for natural cooling till the temperature drops to 15~35° C., and then transfer it into a centrifugal machine for centrifugal separation to obtain secondary semi-finished product, wherein, primary semi-finished product:deionized water:active carbon (weight ratio) =1:1:0.05;

c. Put the secondary semi-finished product into an alcohol washer, input alcohol with mass concentration of over 92%, wash for 0.5~1 hours, then transfer into a centrifugal machine for centrifugal separation to obtain D-glucosamine hydrochloride purified product, wherein, secondary semi-finished product:alcohol (weight ratio)=1:0.5~1.5.

Further, to improve the purity of D-glucosamine hydrochloride, the present invention also includes the following steps to process the D-glucosamine hydrochloride purified product:

(5) Drying: Put the purified product after alcohol washing into a drier, heat it under 0.001 MPa~0.09 Mpa vacuum condition to 40~60° C., dry for 5~6 hours;

(6) Pulverization and packing: Pulverize the dried product to specified mesh number as required, select and pack into D-glucosamine hydrochloride finished product.

Wherein, the citric acid residue in the above Step (1) is citric acid residue from citric acid production by means of fermentation, the dilute alkali in the above Step (2) is sodium hydroxide or ammonium hydroxide solution.

After adoption of the above technical solution, due to recovery of citric acid residue, the environmental pollution caused by the residue is alleviated; Moreover, the D-glucosamine hydrochloride product produced from the raw material of citric acid residue from citric acid production by means of fermentation is vegetarian D-glucosamine hydrochloride, without fishy odor and heavy metal pollution, safe and environment-friendly, with product purity up to 98~102%, and in line with the U.S. Pharmacopeia (USP) $32^{nd}$ edition quality standards; Meanwhile, due to sufficient resources of the raw material, there is no limitation of resources for production, and production cost is low; the present invention further saves the cost to treat environment pollution and has a good effect of recycling economy; More importantly, it overcomes people's bias in this technical field that the reaction temperature must be controlled below 90° C., and enhances product output while ensuring a high product purity. Contrast to more than 10 hours of each reaction period, the present invention reduces the reaction time to in-between 5.5 hours and 2 hours, greatly improving the production efficiency.

DETAIL DESCRIPTION OF PREFERRED EMBODIMENTS

The preferred embodiments of the present invention are described in detailed hereinafter.

Embodiment 1

(1) Hydrolysis: Pump 2000 kg hydrochloride with mass concentration of 30% into the reactor, heat to 65° C. with steam, then input 1000 kg citric acid residue, heat to 100° C. with steam, maintain hydrolysis reaction for 2.5 hours;

(2) Suction filtering: Put the material after the above hydrolysis into a suction filtering barrel for suction filtering, and rinse the filter residue after the suction filtering with running water for twice, and then wash it with dilute alkali of 2% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature drops to 30° C., and then transfer it into a centrifugal machine for centrifugal separation to obtain solid substance, which is crude D-glucosamine hydrochloride;

(4) Purification:

a. Put the post-centrifugation crude product into a primary purifier, input deionized water, heat to 90° C. with steam, input active carbon and maintain reaction for 1 hour, obtain mother solution through suction filtering and transfer it into a primary cooler for natural cooling till the temperature goes down to 30° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 90° C. with steam, input active carbon and maintain reaction for 1 hour, obtain mother solution through suction filtering and transfer it into a secondary cooler for natural cooling till the temperature goes down to 30° C., and then transfer it into a centrifugal machine for centrifugal separation to obtain secondary semi-finished product, wherein, primary semi-finished product: deionized water:active carbon (weight ratio)=1:1:0.05;

c. Put the secondary semi-finished product into an alcohol washer, input alcohol with mass concentration of 92%, wash for 1 hour, then transfer into a centrifugal machine for centrifugal separation to obtain D-glucosamine hydrochloride purified product, wherein, secondary semi-finished product: alcohol (weight ratio)=1:1;

(5) Drying: Put the purified product after alcohol washing into a drier, heat it under 0.05 Mpa vacuum condition to 50° C., dry for 5.5 hours;

(6) Pulverization and packing: Pulverize the dried product to specified mesh number as required, select and pack into D-glucosamine hydrochloride finished product.

The finally obtained D-glucosamine hydrochloride finished product weights 70 kg, with a purity of 99.55%.

Embodiment 2

(1) Hydrolysis: Pump 2250 kg hydrochloride with mass concentration of 35% into the reactor, heat to 60° C. with steam, then input 1000 kg citric acid residue, heat to 105° C. with steam, maintain hydrolysis reaction for 5 hours;

(2) Suction filtering: Put the material after the above hydrolysis into a suction filtering barrel for suction filtering, and rinse the filter residue after the suction filtering with running water for 3 times, and then wash it with dilute alkali of 3% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 25° C., and then transfer it into a centrifugal machine for centrifugal separation to obtain solid substance, i.e., D-glucosamine hydrochloride crude;

(4) Purification:

a. Put the post-centrifugation crude into a primary purifier, input deionized water, heat to 95° C. with steam, input active carbon and maintain reaction for 0.5 hours, obtain mother solution through suction filtering and transfer it into a primary cooler for natural cooling till the temperature goes down to 35° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 95° C. with steam, input active carbon and maintain reaction for 0.5 hours, obtain mother solution through suction filtering and transfer it into a secondary cooler for natural cooling till the temperature goes down to 35° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 95%, wash for 0.8 hours, then transfer into a centrifugal machine for centrifugal separation to obtain D-glucosamine hydrochloride purified product, wherein, secondary semi-finished product:alcohol (weight ratio)=1:0.5;

(5) Drying: Put the purified product after alcohol washing into a drier, heat it under 0.09 Mpa vacuum condition to 60° C., dry for 6 hours;

(6) Pulverization and packing: Pulverize the dried product to specified mesh number as required, select and pack into D-glucosamine hydrochloride finished product.

The finally obtained D-glucosamine hydrochloride finished product weights 78 kg, with a purity of 99.57%.

Embodiment 3

(1) Hydrolysis: Pump 1800 kg hydrochloride with mass concentration of 25% into the reactor, heat to 70° C. with steam, then input 1000 kg citric acid residue, heat to 95° C. with steam, maintain hydrolysis reaction for 2 hours;

(2) Suction filtering: Put the material after the above hydrolysis into a suction filtering barrel for suction filtering, and rinse the filter residue after the suction filtering with running water for twice, and then wash it with dilute alkali of 1% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 25° C., and then transfer it into a centrifugal machine for centrifugal separation to obtain solid substance, which is crude D-glucosamine hydrochloride;

(4) Purification:

a. Put the post-centrifugation crude into a primary purifier, input deionized water, heat to 80° C. with steam, input active carbon and maintain reaction for 1.5 hours, obtain mother solution through suction filtering and transfer it into a primary cooler for natural cooling till the temperature goes down to 25° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 80° C. with steam, input active carbon and maintain reaction for 1.5 hours, obtain mother solution through suction filtering and transfer it into a secondary cooler for natural cooling till the temperature goes down to 20° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 95%, wash for 0.5 hours, then transfer into a centrifugal machine for centrifugal separation to obtain D-glucosamine hydrochloride purified product, wherein, secondary semi-finished product:alcohol (weight ratio)=1:1.5;

(5) Drying: Put the purified product after alcohol washing into a drier, heat it under 0.001 Mpa vacuum condition to 40° C., dry for 5 hours;

(6) Pulverization and packing: Pulverize the dried product to specified mesh number as required, select and pack into D-glucosamine hydrochloride finished product.

The finally obtained D-glucosamine hydrochloride finished product weights 65 kg, with a purity of 99.52%.

Embodiment 4

(1) Hydrolysis: Pump 1600 kg hydrochloride with mass concentration of 35% into the reactor, heat to 68° C. with steam, then input 1000 kg citric acid residue, heat to 90° C. with steam, maintain hydrolysis reaction for 5.5 hours;

(2) Suction filtering: Put the material after the above hydrolysis into a suction filtering barrel for suction filtering, and rinse the filter residue after the suction filtering with running water for 3 times, and then wash it with dilute alkali of 2.5% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 35° C., and then transfer it into a centrifugal machine for centrifugal separation to obtain solid substance, i.e., D-glucosamine hydrochloride crude;

(4) Purification:

a. Put the post-centrifugation crude into a primary purifier, input deionized water, heat to 95° C. with steam, input active carbon and maintain reaction for 1 hour, obtain mother solution through suction filtering and transfer it into a primary cooler for natural cooling till the temperature goes down to 25° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 95° C. with steam, input active carbon and maintain reaction for 1 hour, obtain mother solution through suction filtering and transfer it into a secondary cooler for natural cooling till the temperature goes down to 15° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 92%, wash for 1 hour, then transfer into a centrifugal machine for centrifugal separation to obtain D-glucosamine hydrochloride purified product, wherein, secondary semi-finished product:alcohol (weight ratio)=1:0.8;

(5) Drying: Put the purified product after alcohol washing into a drier, heat it under 0.01 Mpa vacuum condition to 45° C., dry for 6 hours;

(6) Pulverization and packing: Pulverize the dried product to specified mesh number as required, select and pack into D-glucosamine hydrochloride finished product.

The finally obtained D-glucosamine hydrochloride finished product weights 72 kg, with a purity of 99.58%.

Embodiment 5

(1) Hydrolysis: Pump 1900 kg hydrochloride with mass concentration of 30% into the reactor, heat to 70° C. with steam, then input 1000 kg citric acid residue, heat to 98° C. with steam, maintain hydrolysis reaction for 3 hours;

(2) Suction filtering: Put the material after the above hydrolysis into a suction filtering barrel for suction filtering, and rinse the filter residue after the suction filtering with running water for 3 times, and then wash it with dilute alkali of 3% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 30° C., and then transfer it into a centrifugal machine for centrifugal separation to obtain solid substance, i.e., D-glucosamine hydrochloride crude;

(4) Purification:

a. Put the post-centrifugation crude into a primary purifier, input deionized water, heat to 85° C. with steam, input active carbon and maintain reaction for 1.2 hours, obtain mother solution through suction filtering and transfer it into a primary cooler for natural cooling till the temperature goes down to 30° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 90° C. with steam, input active carbon and maintain reaction for 0.3 hours, obtain mother solution through suction filtering and transfer it into a secondary cooler for natural cooling till the temperature goes down to 25° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 95%, wash for 1 hour, then transfer into a centrifugal machine for centrifugal separation to obtain D-glucosamine hydrochloride purified product, wherein, secondary semi-finished product:alcohol (weight ratio)=1:0.5;

(5) Drying: Put the purified product after alcohol washing into a drier, heat it under 0.005 Mpa vacuum condition to 55° C., dry for 5.5 hours;

(6) Pulverization and packing: Pulverize the dried product to specified mesh number as required, select and pack into D-glucosamine hydrochloride finished product.

The finally obtained D-glucosamine hydrochloride finished product weights 68 kg, with a purity of 99.60%.

Embodiment 6

(1) Hydrolysis: Pump 2100 kg hydrochloride with mass concentration of 30% into the reactor, heat to 65° C. with steam, then input 1000 kg citric acid residue, heat to 95° C. with steam, maintain hydrolysis reaction for 3.5 hours;

(2) Suction filtering: Put the material after the above hydrolysis into a suction filtering barrel for suction filtering, and rinse the filter residue after the suction filtering with running water for twice, and then wash it with dilute alkali of 1% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 25° C., and then transfer it into a centrifugal machine for centrifugal separation to obtain solid substance, i.e., D-glucosamine hydrochloride crude;

(4) Purification:

a. Put the post-centrifugation crude into a primary purifier, input deionized water, heat to 90° C. with steam, input active carbon and maintain reaction for 1 hour, obtain mother solution through suction filtering and transfer it into a primary cooler for natural cooling till the temperature goes down to 25° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 85° C. with steam, input active carbon and maintain reaction for 1 hour, obtain mother solution through suction filtering and transfer it into a secondary cooler for natural cooling till the temperature goes down to 25° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 92%, wash for 1 hour, then transfer into a centrifugal machine for centrifugal separation to obtain D-glucosamine hydrochloride purified product, wherein, secondary semi-finished product:alcohol (weight ratio)=1:1.2;

(5) Drying: Put the purified product after alcohol washing into a drier, heat it under 0.05 Mpa vacuum condition to 50° C., dry for 6 hours;

(6) Pulverization and packing: Pulverize the dried product to specified mesh number as required, select and pack into D-glucosamine hydrochloride finished product.

The finally obtained D-glucosamine hydrochloride finished product weights 70.5 kg, with a purity of 99.64%.

Embodiment 7

(1) Hydrolysis: Pump 2300 kg hydrochloride with mass concentration of 25% into the reactor, heat to 75° C. with steam, then input 1000 kg citric acid residue, heat to 100° C. with steam, maintain hydrolysis reaction for 4.5 hours;

(2) Suction filtering: Put the material after the above hydrolysis into a suction filtering barrel for suction filtering, and rinse the filter residue after the suction filtering with running water for 3 times, and then wash it with dilute alkali of 2.5% mass concentration till it becomes neutral or slightly acid, and finally collect the suction filtering mother solution and the washings and mix them;

(3) Concentration: Distill the above mixed mother solution for concentration, stop distillation when the evaporated weight of feed liquid equals 80% of the original mixed mother solution, move the post-distillation mother solution into a cooler for natural cooling till the temperature goes down to 30° C., and then transfer it into a centrifugal machine for centrifugal separation to obtain solid substance, i.e., D-glucosamine hydrochloride crude;

(4) Purification:

a. Put the post-centrifugation crude into a primary purifier, input deionized water, heat to 80° C. with steam, input active carbon and maintain reaction for 1.2 hours, obtain mother solution through suction filtering and transfer it into a primary cooler for natural cooling till the temperature goes down to 30° C., and then transfer it into a centrifugal machine for centrifugal separation to obtain primary semi-finished product, wherein, crude:deionized water:active carbon (weight ratio)=1:1:0.1;

b. Put the above primary semi-finished product into a secondary purifier, input deionized water, heat to 85° C. with steam, input active carbon and maintain reaction for 1 hour, obtain mother solution through suction filtering and transfer it into a secondary cooler for natural cooling till the temperature goes down to 30° C., and then transfer it into a centrifugal machine for centrifugal separation to obtain secondary semi-finished product, wherein, primary semi-finished product:deionized water:active carbon (weight ratio)=1:1:0.05;

c. Put the secondary semi-finished product into an alcohol washer, input alcohol with mass concentration of 99.5%, wash for 0.5 hours, then transfer into a centrifugal machine for centrifugal separation to obtain D-glucosamine hydrochloride purified product, wherein, secondary semi-finished product:alcohol (weight ratio)=1:1;

(5) Drying: Put the purified product after alcohol washing into a drier, heat it under 0.01 Mpa vacuum condition to 55° C., dry for 5 hours;

(6) Pulverization and packing: Pulverize the dried product to specified mesh number as required, select and pack into D-glucosamine hydrochloride finished product.

The finally obtained D-glucosamine hydrochloride finished product weights 73 kg, with a purity of 99.58%.

From Embodiment 1 to 7, the citric acid residues are all citric acid residues from citric acid production by means of fermentation.

After adoption of the above technical solution, due to recovery of citric acid residue, the environmental pollution caused by the residue is alleviated; Moreover, the D-glucosamine hydrochloride product produced from the raw material of citric acid residue from citric acid production by means of fermentation is vegetarian D-glucosamine hydrochloride, without fishy odor and heavy metal pollution, safe and environment-friendly, with product purity up to 98-102%, and in line with the USP32 quality standards; Meanwhile, due to sufficient resources of the raw material, there is no limitation of resources for production, and production cost is low; the present invention further saves the cost to treat environment pollution and has a good effect of recycling economy; More importantly, it overcomes people's bias in this technical field and enhances product output while ensuring a high product purity.

The invention claimed is:

1. A method to prepare D-glucosamine hydrochloride, comprising following steps:

(1) hydrolysis: pump a hydrochloride with introducing hydrochloric acid having a mass concentration of 30% to 35% into a reactor, heating the hydrochloric acid to 60° C. to 70° C. with steam, introducing a citric acid residue into the reactor to form a first mixture, heating the first mixture to 90° C. to 105° C. with steam, maintaining at 90° C. to 105° C. for 2 to 5.5 hours, wherein citric acid residue:hydrochloric acid (weight ratio)=1:1.6 to 2.5;

(2) suction filtering: filtering a material resulting from Step (1) in a suction filtering barrel, and rinsing a filter residue resulting from the suction filtering with running water for 2 to 3 times, and then washing the filter residue with a dilute alkali of 1% to 3% of mass concentration to obtain a neutral or slightly acidic material, and mixing a suction filtering mother solution and washings to obtain a first mother solution;

(3) concentrating: distilling the first mother solution to reduce its weight by 80%, moving the post-distillation first mother solution into a cooler for natural cooling to 25° C. to 35° C., and transfer the cooled solution into a centrifugal machine for centrifugal separation to obtain a solid substance, which is crude D-glucosamine hydrochloride.

2. The method to prepare D-glucosamine hydrochloride as claimed in claim 1, further comprising:

(4) purification:

a. mixing the crude D-glucosamine hydrochloride with deionized water and activated carbon at 80° C. to 95° C. for 0.5 to 1.5 hours to form a second mixture; filtering the second mixture through suction filtering to obtain a second mother solution; cooling the second mother solution to 25° C. to 35° C.; transferring the cooled second mother solution to a centrifugal machine for centrifugal separation to obtain a first purified product, wherein the weight ratio of crude D-glucosamine hydrochloride:deionized water:activated carbon is 1:1:0.1;

b. mixing the first purified product with deionized water and activated carbon at 80° C. to 95° C. for 0.3 to 1.5 hours to form a third mixture; filtering the third mixture through suction filtering to obtain a third mother solution; cooling the second mother solution to 15° C. to 35° C.; transferring the cooled third mother solution to a centrifugal machine for centrifugal separation to obtain a second purified product, wherein the weight ratio of first purified product:deionized water:activated carbon is 1:1:0.05;

c. mixing the second purified product with an alcohol of mass concentration of over 92% for 0.5 to 1 hour to obtain a fourth mixture; transferring the fourth mixture into a centrifugal machine for centrifugal separation to obtain a purified D-glucosamine hydrochloride, wherein the weight ratio of the second purified product:alcohol=1:0.5 to 1.5.

3. The method to prepare D-glucosamine hydrochloride as claimed in claim 2, further comprising:

(5) drying: drying the purified D-glucosamine hydrochloride form Step (4) at 40° C. to 60° C. for 5 to 6 hours under 0.001 MPa to 0.09 MPa vacuum;

(6) pulverizing the dried D-glucosamine hydrochloride from Step (5) to obtain a pulverized D-glucosamine hydrochloride of a predetermined mesh size.

4. The method to prepare D-glucosamine hydrochloride as claimed in claim 1, wherein the citric acid residue in said Step (1) is a citric acid residue from a citric acid production by means of fermentation, and the dilute alkali in said Step (2) is a sodium hydroxide or an ammonium hydroxide solution.

5. The method to prepare D-glucosamine hydrochloride as claimed in claim 2, wherein the citric acid residue in said Step (1) is a citric acid residue from a citric acid production by means of fermentation, and the dilute alkali in said Step (2) is a sodium hydroxide or an ammonium hydroxide solution.

6. The method to prepare D-glucosamine hydrochloride as claimed in claim 3, wherein the citric acid residue in said Step (1) is a citric acid residue from a citric acid production by means of fermentation, and the dilute alkali in said Step (2) is a sodium hydroxide or an ammonium hydroxide solution.

* * * * *